United States Patent [19]

Kozikowski et al.

[11] Patent Number: 5,106,979

[45] Date of Patent: Apr. 21, 1992

[54] METHOD FOR THE SYNTHESIS OF HUPERZINE A AND ANALOGS THEREOF AND COMPOUNDS USEFUL THEREIN

[75] Inventors: Alan P. Kozikowski, Pittsburgh, Pa.; Yan Xia, Baltimore, Md.

[73] Assignee: University of Pittsburgh, Pittsburgh, Pa.

[21] Appl. No.: 499,122

[22] Filed: Mar. 23, 1990

Related U.S. Application Data

[62] Division of Ser. No. 313,118, Feb. 21, 1989, Pat. No. 4,929,731.

[51] Int. Cl.$^5$ .................. C07D 221/22; A01N 43/42; A61K 31/44
[52] U.S. Cl. ......................................... 546/93; 546/97
[58] Field of Search ...................... 546/93, 97; 514/295

[56] References Cited

PUBLICATIONS

C. M. Yu et al., Canadian Journal of Chemistry, 64, 837–839 (1986), The Structures of Huperzine A and B, Two New Alkaloids Exhibiting Marked Anticholinesterase Activity.

D. Gravel et al., Canadian Journal of Chemistry, 62, 2945–2947 (1984), Total Regiospecific Synthesis of Selagine Tricyclic Ring System.

W. Ye et al., Acta Pharmacologica Sinica, 9, 193–196 (1988), Pharmacokinetics of Huperzine A in Rats and Mice.

C. Shi–Ming et al., Acta Pharmaceutica Sinica, 22, 801–806 (1977), The Effects of Fordine on Learning and Memory in Rats.

A. Kende et al., Heterocycles, 21, 91–106, New Tactics in Heterocyclic Synthesis.

Valenta, Z. et al., "Structure of Selagine", CA 54:21167–21168 of Tetrahedron Letters, 1960, No. 10, pp. 26–33.

Chen, C. et al., "Studies on the Bioactive Lyc. Alkaloid", CA 101:143940w of T'ai-wan Yao Hsueh Toa Chih, 1984, vol. 36, #1, pp. 1–7.

Liu(I), "Structure of Huperzine A and B", CA 105:75908x of Can. J. Chem., 1986, vol. 64, #4, pp. 837–839.

Liu(II), "Chemistry of Huperzine A and B", CA107:115821p of Huaxue Xueboo, 1986, vol. 44, #10, pp. 1035–1040.

Yuan, S., et al., "Alkaloids of Huperzia Serrata", CA 110:92014y of Yaoxue Xuebao, 1988, vol. 23, No. 7, pp. 516–520.

Qian, L. et al., "A Total Synthesis of (±) Huperzine A", CA 111:214783s of Tetrahedron Letters, 1989, vol. 30, No. 16, pp. 2089–2090.

Primary Examiner—Robert A. Wax
Assistant Examiner—Fred Tsung
Attorney, Agent, or Firm—Pennie & Edmonds

[57] ABSTRACT

The present invention relates to a method for the synthesis of certain bridged fused ring pyridines. Such bridged fused ring pyridines can be converted to huperzine A and analogs of huperzine A. The present invention also covers such bridged fused ring pyridines, compounds utilized for the preparation of the bridged fused ring pyridines and analogs of huperzine A.

1 Claim, No Drawings

METHOD FOR THE SYNTHESIS OF HUPERZINE A AND ANALOGS THEREOF AND COMPOUNDS USEFUL THEREIN

This invention was made with government support under Grant No. 5 R01 AG07591 awarded by the National Institutes of Health, National Institute of Aging. The government has certain rights in this invention.

This is a division, of application Ser. No. 07/313,118 filed Feb. 21, 1989 now U.S. Pat. No. 4,929,731.

TABLE OF CONTENTS

1. TECHNICAL FIELD
2. BACKGROUND OF THE INVENTION
3. SUMMARY OF THE INVENTION
4. DETAILED DESCRIPTION OF THE INVENTION
   4.1 PREPARATION OF FUSED RING PYRIDINE
   4.2 CONVERSION OF THE BRIDGED FUSED RING PYRIDINE TO HUPERZINE A AND ANALOGS OF HUPERZINE A
5. THE INHIBITION OF CHOLINESTERASE ENZYME
6. EXAMPLES
   6.1 EXAMPLE I—SYNTHESIS OF HUPERZINE A
   6.2 EXAMPLE II—BIOLOGICAL ACTIVITY OF HUPERZINE A AND THE 1-CARBON ANALOG OF HUPERZINE A

1. TECHNICAL FIELD

The present invention relates to a method for the synthesis of certain bridged fused ring pyridines. Such bridged fused ring pyridines can be converted to huperzine A and analogs of huperzine A. The present invention also covers such bridged fused ring pyridines, compounds utilized for the preparation of the bridged fused ring pyridines and analogs of huperzine A.

2. BACKGROUND OF THE INVENTION

Huperzine A, which is a Lycopodium alkaloid, has been isolated from the plant *Huperzia serrata*. It has been shown to inhibit the cholinesterase enzyme and, therefore, has been tested for the treatment of diseases of the cholinergic system. For example, Huperzine A is being studied for the treatment of myasthenia gravis, Alzheimer's dementia and for the improvement of senile memory loss. See J. Liu, et al., *The Structures of Huperzine A and B, Two New Alkaloids Exhibiting Marked Anticholinesterase Activity*, Can. J. Chem., 64, 837–839 (1986).

3. SUMMARY OF THE INVENTION

The present invention relates to a method for the synthesis of a bridged fused ring pyridine of the general formula I:

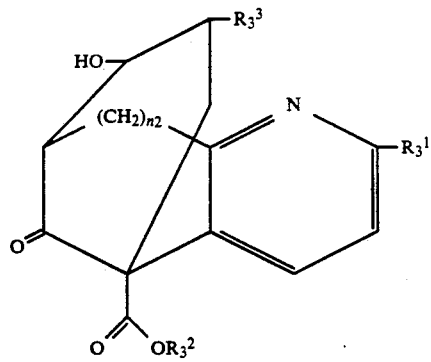

which comprises:

(A) contacting a fused ring pyridine having general formula II:

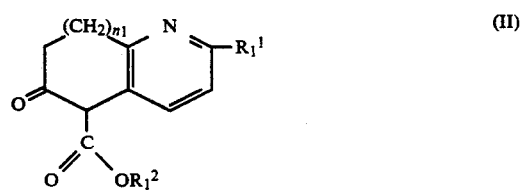

with an unsaturated carbon bridge having the general formula III:

in a suitable solvent comprising an amine base catalyst having a pKa of from about 11 to about 20 to form the bridged fused ring pyridine of general formula I; wherein:

$R_1^1$ is selected from the group consisting of H and $C_1$–$C_8$ linear or branched alkoxy;

$R_1^2$ is selected from the group consisting of $C_1$–$C_8$ linear or branched alkyl;

$R_2^3$ is selected from the group consisting of H and $C_1$–$C_8$ linear or branched alkyl;

$R_3^1$ is selected from the group consisting of H and $C_1$–$C_8$ linear or branched alkoxy;

$R_3^2$ is selected from the group consisting of $C_1$–$C_8$ linear or branched alkyl;

$R_3^3$ is selected from the group consisting of H and $C_1$–$C_8$ linear or branched alkyl;

$n_1$ is an integer from 0 to 4; and $n_2$ is an integer from 0 to 4;

with the proviso:

$R_1^2 = R_3^2$; $R_1^1 = R_3^1$; $R_2^3 = R_3^3$ and $n_1 = n_2$.

The bridged fused ring pyridine of the general formula I can be converted to the compound of general formula IV, which includes huperzine A and the analogs of huperzine A present invention:

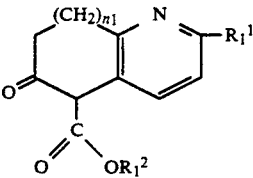

(II)

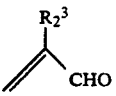

(III)

with an unsaturated carbon bridge having the general formula III:

in suitable solvent comprising an amine base catalyst having a pKa of from about 11 to about 20 to form the bridged fused ring pyridine of general formula I wherein:

$R_1^1$ is selected from the group consisting of H and $C_1$-$C_8$ linear or branched alkoxy;

$R_1^2$ is selected from the group consisting of $C_1$-$C_8$ linear or branched alkyl;

$R_2^3$ is selected from the group consisting of H and $C_1$-$C_8$ linear or branched alkyl;

$R_3^1$ is selected from the group consisting of H and $C_1$-$C_8$ linear or branched alkoxy;

$R_3^2$ is selected from the group consisting of $C_1$-$C_8$ linear or branched alkyl;

$R_3^3$ is selected from the group consisting of H and $C_1$-$C_8$ linear or branched alkyl;

$n_1$ is an integer from 0 to 4; and $n_2$ is an integer from 0 to 4;

with the proviso:

$R_1^2 = R_3^2$; $R_1^1 = R_3^1$; $R_2^3 = R_3^3$ and $n_1 = n_2$.

In a preferred embodiment:

$R_1^1$ is OCH$_3$;

$R_1^2$ is —CH$_3$;

$R_2^3$ is CH$_3$;

$R_3^1$ is OCH$_3$;

$R_3^2$ is CH$_3$;

$R_3^3$ is CH$_3$;

$n_1$ is 1; and $n_2$ is 1. This embodiment is preferred because with such embodiment huperzine A can be readily made.

It has now been discovered that the use of a suitable solvent comprising an amine base catalyst having a pKa of from about 11 to about 20 readily permits (>90% yield) the unsaturated carbon bridge of general formula III to be readily added to the fused ring pyridine of general formula II. Without being bound by theory, it is believed that the unsaturated carbon bridge is added to the fused ring pyridine by Michael reaction followed by an aldol reaction.

It is believed that the use of the amine base catalyst having a pKa of from about 11 to about 20, and preferably about 14, is what permits such reaction to proceed so readily. (Such pKa is measured relative to water.) For example, the amine base catalyst triethylamine, whose pKa is about 10, fails to permit the reaction to proceed. Also, the base catalyst sodium methoxide, which is not an amine base catalyst, but has a pKa of about 16, also does not permit the reaction to proceed.

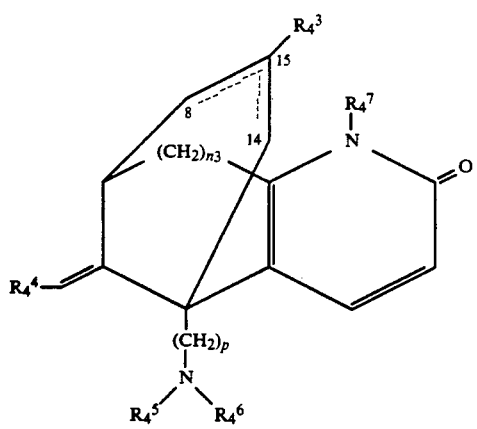

(IV)

wherein:

$R_4^3$ is selected from the group consisting of H and $C_1$-$C_8$ linear or branched alkyl;

$R_4^4$ is selected from the group consisting of H and $C_1$-$C_8$ linear or branched alkyl;

$R_4^5$ is selected from the group consisting of H and $C_1$-$C_8$ linear or branched alkyl;

$R_4^6$ is selected from the group consisting of H and $C_1$-$C_8$ linear or branched alkyl;

$R_4^7$ is selected from the group consisting of H and $C_1$-$C_8$ linear of branched alkyl;

$n_3$ is an integer from 0 to 4;

p is 0 or 1;

- - - - - represents a double bond between carbon 14 and 15 or a double bond between carbon 8 and 15;

with the proviso: $R_2^3 = R_3^3 = R_4^3$.

The compounds of general formula IV are capable of inhibiting the cholinesterase enzymes.

4. DETAILED DESCRIPTION OF THE INVENTION

The present invention relates to a method for the synthesis of a bridged fused ring pyridine of general formula I:

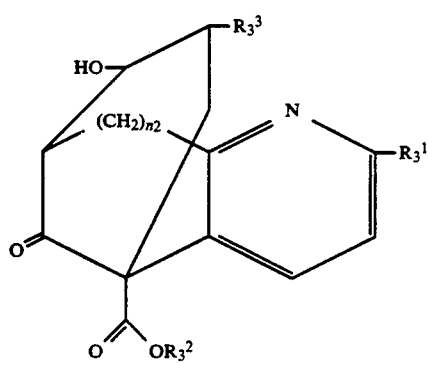

(I)

The method comprises contacting a fused ring pyridine of the general formula II:

Preferred amine base catalysts are 1,1,3,3-tetramethylguanidine (TMG) and diazabicycloundecene, with TMG being most preferred.

It is believed that any suitable solvent that permits the reaction to proceed can be utilized, but a polar solvent is preferred and a polar aprotic solvent is even more preferred. Examples of polar aprotic solvents are methylene chloride, chloroform, dimethylformamide, dimethyl sulfoxide, and tetrahydrofuran (THF), with methylene chloride being preferred.

It should be noted that no stereochemistry is implied by the general formulas utilized in the present invention; all stereoisomers are included in each general formula.

4.1 PREPARATION OF FUSED RING PYRIDINE

The fused ring pyridine of general formula II can be prepared by utilizing SCHEME I, below.

The starting material is a monoprotected diketone 1. The monoprotected diketone 1 is reacted with pyrrolidine and resulting enamine is heated with acrylamide to provide the lactam 2. The lactam intermediate is then converted by a dehydrogenation procedure to the pyridone 3. Next, this pyridone is alkylated on oxygen to provide the alkoxypyridine derivative 4($R^1$=OR). The ketone carbonyl group is now deprotected and an α-carboalkoxylation reaction is carried out to provide the β-keto ester material 5, which corresponds to a molecule of general formula II.

Pyridone 3 can also be converted to a fused ring pyridine of general formula II (or 5) with $R^1$=H by reducing the pyridone carbonyl group of 3 to hydroxyl and carrying out a subsequent dehydration step. Removal of the ketal protecting group and a carboalkoxylation reaction the provide II (or 5) with $R^1$=H.

SCHEME I

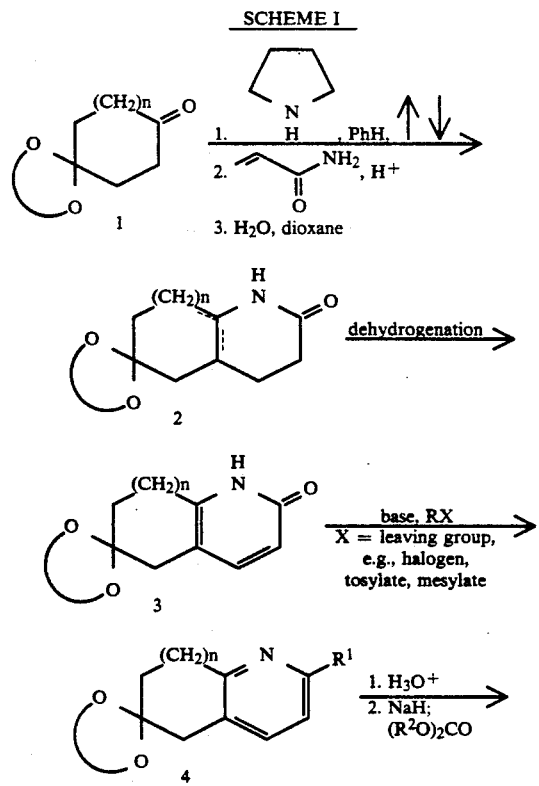

-continued
SCHEME I

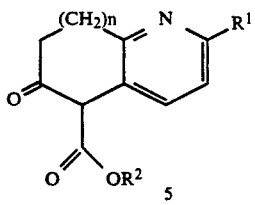

4.2. CONVERSION OF THE BRIDGED FUSED RING PYRIDINE TO HUPERZINE A AND ANALOGS OF HUPERZINE A

The bridged fused ring pyridine of general formula I can be converted to a compound of general formula IV, which includes huperzine A and the analogs of huperzine A of the invention:

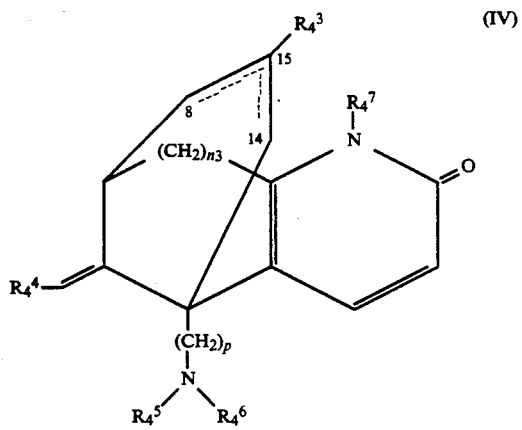

wherein:

$R_4^2$ is selected from the group consisting of H and $C_1$-$C_8$ linear or branched alkyl;

$R_4^4$ is selected from the group consisting of H and $C_1$-$C_8$ linear or branched alkyl;

$R_4^5$ is selected from the group consisting of H and $C_1$-$C_8$ linear or branched alkyl;

$R_4^6$ is selected from the group consisting of H and $C_1$-$C_8$ linear or branched alkyl;

$R_4^7$ is selected from the group consisting of H and $C_1$-C linear of branched alkyl;

$n_3$ is an integer from 0 to 4;

p is 0 or 1;

------ represents a double bond between carbon 14 and 15 or a double bond between carbon 8 and 15;

with the proviso: $R_2^3 = R_3^3 = R_4^3$.

Since huperzine A is the preferred compound to synthesize, preferably:

$R_4^3$ is $CH_3$;

$R_4^4$ is $CH_3$;

$R_4^5$ is H;

$R_4^6$ is H;

$R_4^7$ is H;

$n_3$ is 1;

p is 0

------ represents a double bond between carbon 8 and 15.

Even more preferred of such preferred embodiment is the E-stereoisomer of general formula IV, which represents huperzine A.

The compounds of general formula IV can be prepared by utilizing scheme II, hereinbelow.

The bridged fused ring pyridine 6 is converted to the bridged ketone 7 by various dehydrating conditions. It is preferred that the alcohol is activated for elimination by transformation to its mesylate derivative, which is then heated in sodium acetate and acetic acid to provide the bridged ketone 7.

The bridged ketone 7 is then reacted with the desired alkylidenephosphorane ($Ph_3P$=$CHR^4$ wherein $R^4$ is H or a $C_1$-$C_8$ linear or branched alkyl) in a suitable solvent, e.g. tetrahydrofuran or ether, to provide the olefin 8 (note: where $R^4$ is alkyl, a cis/trans mixture is formed). To obtain the olefinic product of predominantly E-stereochemistry, a thermal isomerization reaction employing thiophenol and azoisobutyronitrile (AIBN) can be carried out to form ester 9.

The ester 9 is then transformed to the urethane derivative 10 by carrying out a standard Curtius reaction, which comprises hydrolyzing the ester to its acid, converting the acid to an acid chloride, followed by heating the acid chloride with sodium azide and then with methanol.

Urethane 10 can then be converted to amine 11 (huperzine A if $R^3$=$R^4$=$CH_3$ and n=1) by effecting cleavage of both the alkyl group $R^1$ (where $R^1$=OR) and the carbomethoxy group by reacting urethane 10 with a dealkylating agent, e.g. trimethylsilyl iodide.

In cases where $R^1$ in the accompanying structures is H, the pyridine ring is generated from the pyridone ring by a process involving pyridine N-oxide formation by use of a peracid, treatment with acetic anhydride, and then acid hydrolysis [M. Katada, J. Pharm. Soc. Japan, 67, 51 (1947)]. This conversion step is best performed prior to the TMSI promoted cleavage of the urethane and can be performed at an earlier stage if required. Some modification may be required to avoid competing olefin epoxidation and/or oxidation of the acyclic amino group.

To procure the N-alkyl amino substituted derivatives 13 of huperzine A, the carbomethoxy group of 10 is removed by base hydrolysis, and the resulting free amine is sequentially alkylated to introduce $R^5$ and $R^6$ or $R^5$ alone. An appropriate alkyl halide or tosylate, or a reductive amination procedure is employed in introducing these groups. Lastly, the alkoxypyridine intermediate 12 (where $R^1$=OR) is cleaved to the pyridone 13 by O-dealkylation using a reagent such as TMSI.

Another aspect of the present invention is the pyridine intermediate 12 having the general formula V:

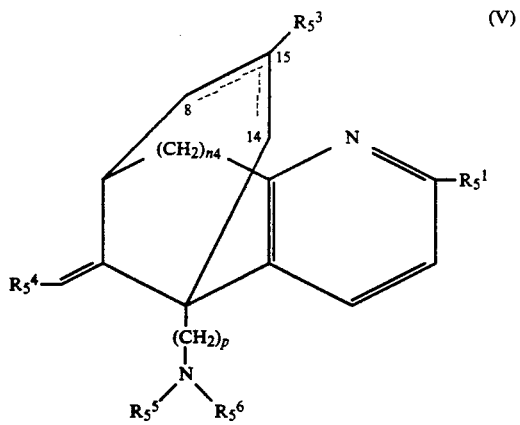

wherein:
$R_5^1$ is selected from the group consisting of H and $C_1$-$C_8$ linear or branched alkoxy;
$R_5^3$ is selected from the group consisting of H and $C_1$-$C_8$ linear or branched alkyl;
$R_5^4$ is selected from the group consisting of H and $C_1$-$C_8$ linear or branched alkyl;
$R_5^5$ is selected from the group consisting of H and $C_1$-$C_8$ linear or branched alkyl;
$R_5^6$ is selected from the group consisting of H and $C_1$-$C_8$ linear or branched alkyl;
$n_4$ is an integer from 0 to 4;
p is 0 or 1;
represents a double bond between carbon 14 and 15 or a double bond between carbon 8 and 15.

Since huperzine A is the preferred compound to synthesize, preferably:
$R_5^1$ is $OCH_3$;
$R_5^3$ is $CH_3$;
$R_4^4$ is $CH_3$;
$R_5^5$ is H;
$R_5^6$ is H;
$n_4$ is 1;
p is 0; and
represents a double bond between carbon 8 and 15.

Even more preferred of such preferred embodiment is the E-stereoisomer of general formula V, which is capable of being converted to huperzine A.

To obtain the huperzine analogs 14 containing an alkyl group ($R^7$) on the pyridine ring nitrogen, intermediate 13 is deprotonated with a base and the resulting anion is reacted with $R^7X$, where X is some suitable leaving group such as tosylate, mesylate, or halide.

To obtain the double bond regioisomer 16 of huperzine A, the double bond of 7 is subjected to an olefin isomerization reaction using a suitable metal catalyst (e.g., $Fe(CO)_5$, $(Ph_3P)_4Ru(MeCN)$, $HCo(CO)_4$), or by hydrating the double bond of 7 in the Markovnikov sense ($H^+$, $H_2O$), and then carrying out a subsequent dehydration reaction.

The intermediate 15 is then used in the place of 7 in the foregoing reactions to provide the double bond regiosomers of 11, 13, and 14.

Saturated analogs 18 of huperzine A are readily obtained by subjecting 6 to a Barton deoxygenation procedure [the alcohol is converted to its thiocarbonyl ester, and a tin hydride reduction carried out; see D. H. R. Barton and W. B. Motherwell, Pure Appl. Chem., 53, 15 (1981)]. Intermediate 17 is then carried through reaction steps identical to those employed above for the conversion of 7 to 11, 13, or 14 in order to acquire the saturated analogs 18 of huperzine A.

The one carbon homologs 20 of huperzine A can be obtained from 9 by reduction of ester to alcohol, conversion of alcohol to azide, and reduction of the azide to amine with LAH to afford 19. The alkoxypyridine intermediate 19 (where $R^1$=OR) is then transformed to 20 by O-dealkylation using a reagent such as TMSI. Amine alkylation procedures like those described for the conversion of 10 to 13 and 13 to 14 can be employed to procure the analog 21. By starting with 15 and carrying out a similar sequence of reactions to those described hereinabove beginning with a Wittig step, access to the homolog 22 (a double bond regioisomer of 21) can be achieved.

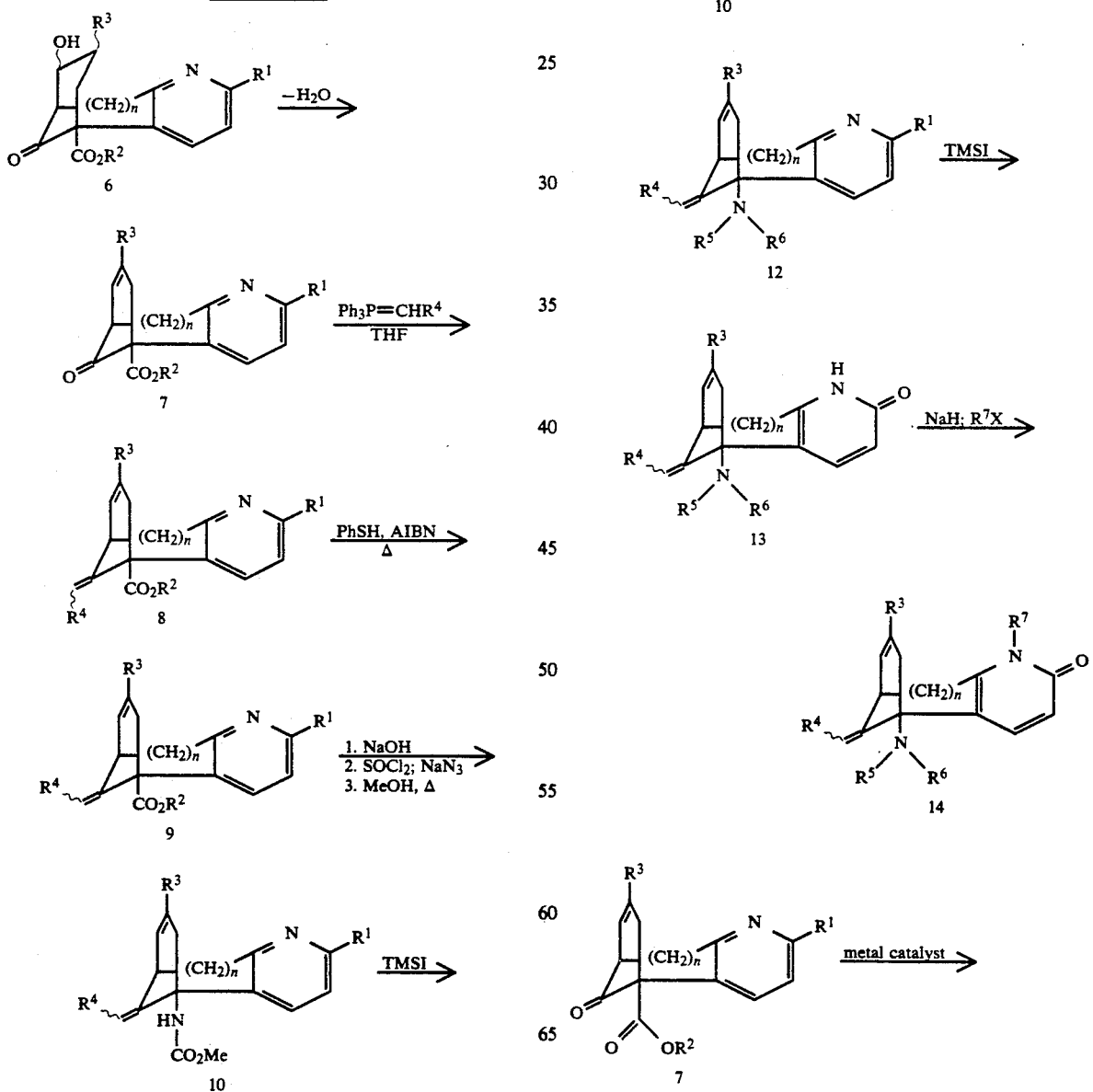

SCHEME II

-continued
SCHEME II

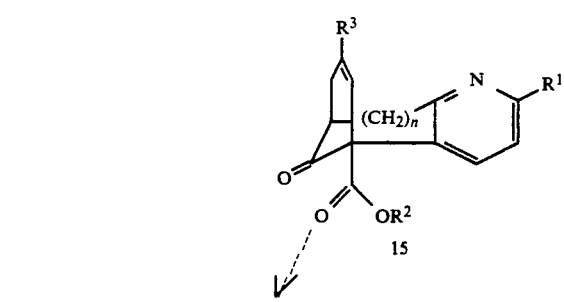
15

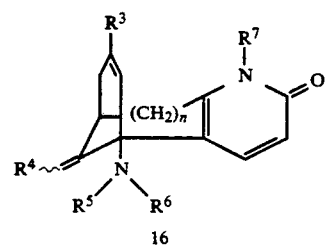
16

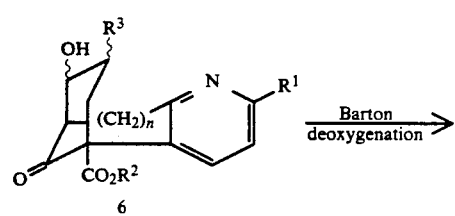 Barton deoxygenation →
6

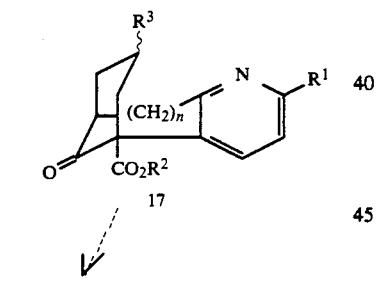
17

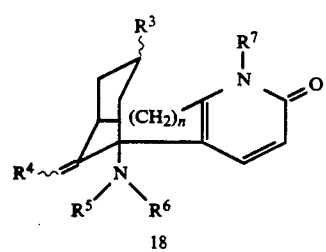
18

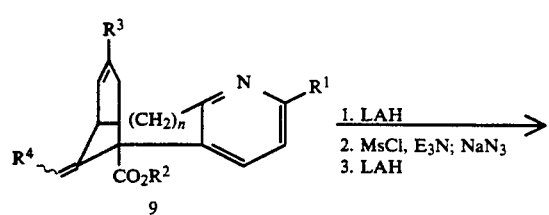
1. LAH
2. MsCl, E₃N; NaN₃
3. LAH →
9

-continued
SCHEME II

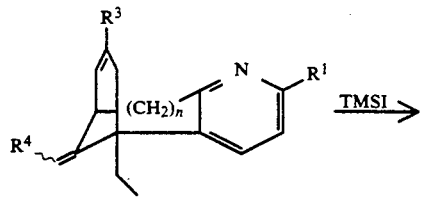 TMSI →
19

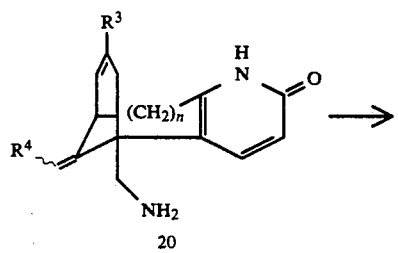 →
20

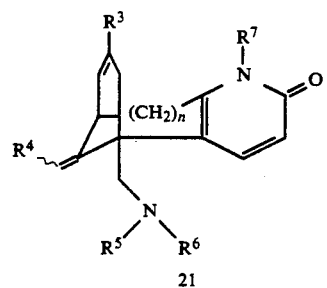
21

15 → 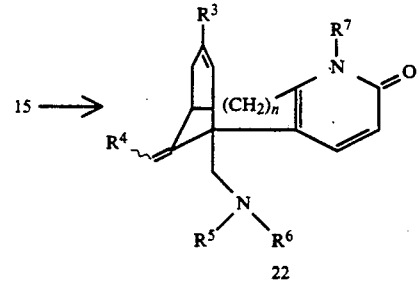
22

5. THE INHIBITION OF CHOLINESTERASE ENZYMES

The compounds of general formula IV are capable of inhibiting the cholinesterase enzymes and, therefore, are useful as pharmaceutical agents for mammals, especially for humans, for the treatment of disorders wherein cholinesterase enzymes are involved. Examples of such disorders are myasthenia gravis, Alzheimer's dementia and the improvement of senile memory loss.

The compounds of general formula IV can be administered to a human subject either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of a compound of general formula IV, such compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparations isotonic.

When a compound according to general formula IV is used as in a human subject, the daily dosage will normally be determined by the prescribing physician with the dosage generally varying according to the age, weight, and response of the individual patient, as well as the severity of the patient's symptoms. However, in most instances, an effective daily dosage will be in the range of from about 0.05 mg/kg to about 1 mg/kg of body weight, and preferably, of from 0.1 mg/kg to about 0.5 mg/kg of body weight, administered in single or divided doses. In some cases, however, it may be necessary to use dosages outside these limits.

EXAMPLES

It should be noted that in the examples the numbers following the named compounds refer to the numbered compounds of Scheme I and Scheme II. Also, the variables stated in the examples correspond to the variables of the general formulas.

6.1 EXAMPLE I

Synthesis of Huperzine A

Preparation of Lactam 2 (n=1)

In a 500 mL round-bottomed flask equipped with a water separator and a condenser were placed 25 g (0.16 mol) of 1,4-cyclohexanedione monoethylene ketal, 27 mL (0.32 mol) of pyrrolidine, 1 g of p-toluenesulphonic acid, and 250 mL of benzene. The mixture was refluxed until no more water separated in the water separator. Benzene was evaporated and the residue was dissolved in 250 mL of dioxane. To this solution was added 34 g (0.48 mol) of acrylamide and the mixture was refluxed overnight. Water (100 mL) was added and the solution was refluxed for 12 h. After cooling down to room temperature, the dioxane was removed by rotary evaporation and the aqueous residue was extracted with $CHCl_3$. The extracts were washed with brine, dried with anhydrous $MgSO_4$, and filtered. After evaporation of the solvent, the residue was chromatographed on silica gel with ethyl acetate as the eluent. The yield was 20 g (59%).

Preparation of Pyridine 3

(1.) N- Benzylation of 2 (n=1)

Potassium hydride (1.38 g, 0.0348 mol) was added in several portions to a mixture of the lactams 2 and 3 (4.85 g, 0.023 mol), benzyl chloride (5.3 mL, 0.0464 mol), and a catalytic amount of tetrabutylammonium iodide in 250 ml of dry THF. The mixture was stirred at room temperature overnight with the protection of a drying tube. Water was added dropwise to quench the excess KH, and the THF was removed by rotary evaporation. The aqueous residue was extracted with ethyl acetate. The extracts were washed with brine, dried with anhydrous $MgSO_4$, and filtered. Evaporation of the solvent, and purification of the residue by flash chromatography (ethyl acetate gave 6.95 g of the N-benzylated product (quantitative yield).

(2.) Dehydrogenation of the N-benzylated product

To a solution of diisopropylamine (6.2 mL, 0.044 mol) in 100 mL of dry THF at 0° C. under $N_2$ was added n-BuLi (24 mL of 1.6M n-BuLi in hexanes, 0.038 mol). The solution was stirred at 0° C. for 20 min. and then cooled to $-78°$ C. A solution of the above benzyl protected lactams (3.80 g, 0.0127 mol) in 100 mL of dry THF was added at $-78°$ C. The color of the reaction mixture immediately turned deep blue. After stirring at $-78°$ C. for 2 h, a solution of phenylselenyl chloride (4.87 g, 0.0254 mol) in 20 mL of dry THF was added dropwise, and the resulting solution was stirred at $-78°$ C. for 15 min.

The solution was quenched with methanol (20 mL) and allowed to warm to room temperature. The solution was then poured into a mixture of $NaIO_4$ (10.88 g, 0.051 mol) in 300 mL of $H_2O$-MeOH-THF (1:1:1). Another 100 mL of THF was used to rinse the reaction flask and combined with the above mixture. The mixture was stirred at room temperature for 24 h.

THF and methanol were removed by rotary evaporation, and the aqueous residue was extracted with ethyl acetate. Concentration of the ethyl acetate solution gave a red syrup. The syrup was dissolved in 100 mL of MeOH. $Et_3N$ (1.8 mL, 0.0127 mol) was added, and the solution was refluxed overnight. Concentration and column chromatography (ethyl acetate) gave 2.78 (74%) of the N-benzyl derivative of 3 as a red syrup.

(3.) Hydrogenolysis of the N-benzyl derivative of 3

The benzyl protected pyridone 4 (1.33 g, 4.48 mmol) was stirred with $Pd(OH)_2$ 20 wt. %) in acetic acid under a $H_2$-filled balloon at room temperature overnight. The solution was filtered and the acetic acid solvent was removed by rotary evaporation. Toluene was added to the residue, and the solution was again evaporated to remove the remaining acetic acid. The crude product (80%) was used directly in the following O-methylation reaction.

Preparation of Methoxypyridine 4 (n=1, $R^1$=$OCH_3$)

The crude pyridone ( 80%×4.48 mmol) was stirred with a mixture of $Ag_2CO_3$ (2 mol equivalent), iodomethane (10 mol equivalent), and chloroform (50 mL) in the dark at room temperature overnight. Filtration, concentration and silica gel chromatography (40% ethyl acetate/hexanes as eluent) gave 0.74 g (75% for the two steps) of product 5.

Preparation of β-Keto Ester 5 (n=1, $R^1$=$OCH_3$)

(1) The ketal 4(1.71 g) was refluxed in 5% HCl-acetone (1:1) overnight. Acetone was removed on a rotary evaporator and the aqueous layer was basified with solid $NaHCO_3$. The resulting mixture was extracted with ethyl acetate. The organic extracts were washed with brine, dried over anhydrous $MgSO_4$, and filtered. Concentration and flash chromatography (30% ethyl acetate/hexanes) gave 1.16 g (85%) of the product as a sticky solid.

(2) The above ketone (1.16 g, 6.55 mmol) in 10 mL of dimethyl carbonate was added dropwise to a mixture of KH (1.05 g, 26.2 mmol) in 40 mL of dimethyl carbonate under nitrogen at room temperature. The mixture was refluxed for 3 h. The reaction was quenched with methanol, and the solution was neutralized with a saturated NH$_4$Cl solution. The methanol was removed by rotary evaporation, and the aqueous residue was extracted with ethyl acetate. The ethyl acetate extracts were washed with brine, dried over anhydrous MgSO$_4$, and filtered. Concentration and flash chromatography (20% ethyl acetate/hexanes) gave 1.34 g (87%) of 5 as a solid.

Preparation of Bridged Adduct 6 (n=1, R$^1$=OCH$_3$, R$^2$=R$^3$=CH$_3$)

The β-keto ester 5(502 mg, 2.15 mmol) was stirred with methacrolein (1.76 mL, 21.4 mmol) and 1,1,3,3-tetramethylguanidine (54 μL, 0.42 mmol) in dry CH$_2$Cl$_2$ at room temperature overnight. Concentration and flash chromatography (40% ethyl acetate/hexanes) gave 604 mg (93%) of the bridged adduct 6.

Dehydration of Alcohol 6

(1) Mesyl chloride (1.89 mL, 24.5 mmol) was added dropwise to a solution of the alcohol 6(1.87 g, 6.13 mmol), triethylamine (8.46 mL, 61.3 mmol), and a catalytic amount of 4-N,N-dimethylaminopyridine in 50 mL of dry CH$_2$Cl$_2$ at room temperature. The solution was stirred for 6 h at room temperature. The solution was diluted with CH$_2$Cl$_2$, washed with NH$_4$Cl (sat.), dried, and concentrated to give 2.26 g (96%) of the crude mesylate.

(2) The crude mesylate (2.26 g, 5.90 mmol) was heated with anhydrous NaOAc (0.48 g, 5.9 mmol) in AcOH at 120°C. under N$_2$ for 24 h. The acetic acid was removed by rotary evaporation at 50° C. The residue was dissolved in ethyl acetate, washed with saturated Na$_2$CO$_3$ and brine, and dried. Evaporation of the ethyl acetate and flash chromatography of the residue (20% and then 40% ethyl acetate/hexanes) gave 521 mg (31% or 47% based on 66% conversion) of 7 as a solid and 0.76 g (34%) of the starting material.

Wittig Reaction of β-Keto Ester 7 (n=1,R$^1$=OCH$_3$, R$^2$=R$^3$=CH$_3$)

n-BuLi (2.57 mL, 3.80 mmol) was added dropwise to a mixture of ethyltriphenylphosphonium bromide (1.59 g, 4.28 mmol) in 15 mL of dry THF at room temperature under nitrogen. The reaction mixture was stirred at room temperature for 30 min. and then cooled to 0° C. The ketone (273 mg, 0.951 mmol) in 5 mL of dry THF was added dropwise to this mixture at 0° C. The resulting mixture was allowed to warm to room temperature, and stirred at room temperature for 4 h. The reaction was quenched with water. The THF was removed by rotary evaporation, and the aqueous residue was extracted with ethyl acetate. The ethyl acetate extracts were washed with brine, dried, and concentrated. Flash chromatography (10% ethyl acetate/hexanes gave 208 mg (73%) of olefin 8 as a 10:90 E/Z-mixture.

Isomerization of the Olefin Mixture
8(n=1,R$^1$=OCH$_3$,R$^2$=R$^3$=R$^4$=CH$_3$)

The olefin 8 (79 mg, 0.26 mmol) was heated with azoisobutyronitrile (87 mg, 0.52 mmol) in 10 mL of thiophenol at 130° C. under nitrogen for 24 h. The solution was cooled, diluted with CH$_2$Cl$_2$, and washed with 10% NaOH (5 times) and brine. After drying and concentration, the crude product was used directly in the next hydrolysis reaction. $^1$H NMR analysis revealed olefin 9 to be comprised of an 80/20 mixture of the E and Z-alkenes, respectively.

Preparation of Carbamate 10 (n=1, R$^1$=OCH$_3$, R$^2$=R$^3$=CH$_3$)

The crude ester (0.26 mmol, E/Z =80/20) was dissolved in a 1:1 mixture of 20% NaOH and THF. Enough MeOH was added to convert the heterogeneous mixture to a homogenous one, and this solution was refluxed under nitrogen for 2 days. THF and MeOH were removed by rotary evaporation, and the aqueous residue was extracted with CH$_2$Cl$_2$. These organic extracts were washed with brine, dried, and concentrated to give the unhydrolyzed Z-ester which can be recycled through the isomerization step. The aqueous residue was adjusted to a pH of 7 with concentrated HCl. Extraction with CH$_2$Cl$_2$, drying, and concentration gave the crude acid which was further purified by column chromatography (20% ethyl acetate/hexanes and then ethyl acetate) to afford 36 mg (61% based on the E-ester) of pure acid.

Thionyl chloride (51μ, 0.65 mmol) was added dropwise to a solution of the acid (36 mg 0.13 mmol) in 5 mL of toluene under nitrogen at room temperature. The solution was heated at 80° C. for 2 h, and then cooled to room temperature. Sodium azide (82 mg, 1.3 mmol) was added, and the mixture was heated at 80° C. overnight. The toluene was removed by rotary evaporation, 5 mL of MeOH was added, and the resulting mixture was refluxed for 8 h. The methanol was removed by rotary evaporation, and the residue was dissolved in ethyl acetate. The solution was washed with brine, dried, and concentrated. Flash chromatography (20% ethyl acetate/hexanes) gave 15 mg (37%) of the urethane 10.

Huperzine A

Iodotrimethylsilane (50 μM, 0.35 mmol) was added dropwise to a solution of the carbamate 10 (7 mg, 0.02 mmol) in 2 mL of chloroform under nitrogen at room temperature. The solution was then refluxed overnight. Methanol (2 mL) was added, and the solution was refluxed for an additional 2 h. Concentration and flash chromatography on silica gel half-saturated with ammonia (3% methanol in chloroform) gave 4 mg (70%) of huperzine A along with 2 mg (30%) of the partially deprotected carbamate.

The following is the spectral data for EXAMPLE I:
2 (isomer ratio=85/15): R$_f$=0.30 (ethyl acetate); IR 2900–3700 (br.), 3211, 3063, 2951, 1676, 1473, 1392, 1340, 1255, 1213, 1126, 1097, 1061, 1020, 993, 947, 920, 733 cm$^{-1}$; $^1$H NMR δ8.45 (br. s, 0.85 H), 7.73 (br. s, 0.15 H), 4.83–4.87 (m, 0.85 H), 3.90–4.03 (m, 4 H), 1.51–2.56 (four groups of multiplets, 9.15 H); mass spectrum (m/z) 209 (M$^+$), 123, 86, exact mass calcd. for C$_{11}$H$_{15}$NO$_3$ 209.1052, found 209.1051.

N-Benzyl derivative of 2: (isomer ratio=70/30): R$_f$=0.46 (ethyl acetate); IR 2949, 2889, 1668, 1645, 1496, 1454, 1429, 1396, 1375, 1286, 1192, 1145, 1101, 1061, 1026, 947, 698 cm$^{-1}$; $^1$H NMR δ7.13–7.32 (m, 5H), 5.41 (d, 0.7 H, J=16.1 Hz), 4.84–4.87 (m 1.3 H), 4.50 (d. 0.7 H, J=16.1 Hz), 3.91–4.03 (m, 4 H), 1.58-2.81 (four groups of multiplets, 9.3 H); mass spectrum (m/z) 299 (M$^+$), 213, 185, 91, exact mass calcd. for C$_{18}$H$_{21}$NO$_3$ 299.1521, found 299.1521.

N-Benzyl derivative of Pyridine 3: R$_f$=0.17 (ethyl acetate); IR 2957, 2887, 1664, 1593, 1545, 1496, 1454, 1419, 1398, 1373, 1269, 1228, 1207, 1167, 1113, 1062, 1028, 947, 862, 827, 733, 702 cm$^{-1}$; $^1$H NMR$\delta$7.06-7.34 (m, 6 H), 6.57 (d, 1H, J=9.3 Hz), 5.34 (s 2 H), 3.97-4.02 (m, 4 H), 2.80 (t, 2 H, J=6.6 Hz), 2.73 (s, 2 H), 1.83 (t, 2H, J =6.7 Hz); mass spectrum (m/z) 297 (M+), 206, 134, 91, exact mass calcd for C$_{18}$H$_{19}$NO$_3$ 297.1365, found 297.1364.

3: mp=dec. above 250° C., IR 2930, 1639, 1620, 554, 1506, 1464, 1446, 1379, 1269, 1130, 1097, 1061, 1014, 949, 837, 696 cm$^{-1}$; $^1$H NMR$\delta$12.56 (br. s, 1 H), 7.14 (d, 1H, J=9.3 HZ), 6.40 (d, 1 H, J=9.3 Hz), 4.02 (s, 4 H), 2.89 (t, 2 H, J=6.6 Hz), 2.71 (s, 2 H), 1.93 t, 2H, J=6.6 Hz), $^{13}$C NMR$\delta$165.0, 143.4, 141.8, 117.3, 111.9, 107.3, 64.6, 36.2, 30.1, 25.7; mass spectrum (m/Z) 207 (M+), 164, 134, 86, 69, 57, exact mass calcd for C$_{11}$H$_{13}$NO$_3$ 207.0895, found 207.0896.

4: mp=77.5°-78.5° C.; R$_f$=0.48 (40% ethyl acetate in hexanes); IR 2942, 2885, 1601, 1581, 1478, 1466, 1457, 1429, 1420, 1313, 1259, 1120, 1094, 1061, 1032, 1018, 947, 817 cm$^{-1}$; $^1$H NMR$\delta$7.22 (d, 1 H, J=8.3 Hz), 6.52 (d, 1 H, J=8.3 Hz), 4.03 (s, 4 H), 3.88 (s, 3 H), 3.01 (t, 2 H, J=6.8 Hz), 2.89 (s, 2 H), 2.01 (t, 2H, J=6.8 Hz); mass spectrum (m/z) 221 (M+), 148, 134, 64, exact mass calcd for C$_{12}$H$_{15}$NO$_3$ 221.1052, found 221.1053.

Ketone derived from 4: R$_f$=0.44 (40% ethyl acetate in hexanes); IR 2945, 2916, 2891, 1712, 1604, 1582, 1482, 1430, 1337, 1318, 1309, 1296, 1267, 1195, 1188, 1182, 1166, 1108, 1032, 859, 825 cm$^{-1}$; $^1$H NMR$\delta$7.30 (d, 1 H, J=8.3 Hz), 6.61 (d, 1 H, J=8.3 Hz), 3.93 (s, 3 H), 3.51 (s, 2 H), 3.16 (t, 2 H, J=6.9 Hz), 2.66 (t, 2 H, J=6.9 Hz); $^{13}$C NMR$\delta$209.4, 162.7, 153.5, 138.8, 120.2, 108.8, 53.4, 42.5, 38.0, 30.9; mass spectrum (m/z) 177 (M+), 162, 148, 106, exact mass calcd for C$_{10}$H$_{11}$NO$_2$ 177.0790, found 177.0790.

5: R$_f$=0.33 (20% ethyl acetate in hexanes); IR 2954, 2895, 2837, 1641, 1603, 1568, 1477, 1448, 1427, 1317, 1263, 1226, 1116, 1059, 1035, 1016, 941, 918, 825, 785, 640, 625 cm$^{-1}$; $^1$H NMR$\delta$13.16 (s, 1 H), 7.90 (d, 1 H, J=8.7 Hz), 6.56 (d, 1 H, J=8.7 Hz), 3.91 (s, 3 H), 3.90 (s, 3 H), 2.94 (t, 2 H, J =8.7 Hz), 6.56 (d, 1 H, J=8.7 Hz), 3.91 (s, 3H), 3.90 (s, 3 H), 2.94 (t, 2 H, J=7.8 Hz), 6.56 (d, 1 H, J=8.7 Hz), 3.91 (s, 3 H), 3.90 (s, 3 H), 2.94 (t, 2 H, J=7.8 Hz), 2.63 (t, 2 H, J=7.8 Hz); $^{13}$C NMR$\delta$176.7, 171.9, 161.1, 151.1, 136.1, 119.8, 107.2, 98.2, 53.3, 51.7, 29.9, 29.0; mass spectrum (m/z) 235 (M+), 203, 148, exact mass calcd for C$_{12}$H$_{13}$NO$_4$ 235.0845, found 235.0845.

6: R$_f$=0.30-0.35 (40% ethyl acetate in hexanes); IR 3100-3600 (br), 2953, 1743, 1603, 1576, 1481, 1423, 1325, 1269, 1155, 1118, 1078, 1034, 983, 827, 758 cm$^{-1}$; $^1$H NMR (one of the isomers)$\delta$7.02 (d, 1 H, J=8.6 Hz), 6.60 (d, 1 H, J=8.6 Hz), 3.91 (s, 3 H), 3.81 (s, 3 H), 3.62-3.69 (m, 2 H), 3.03-3.25 (m, 2H), 2.23 (br. s, —OH), 1.98-2.04 (m, 2 H), 1.48-1.59 (m, 1H), 1.03 (d, 3 H, J=6.4 Hz), mass spectrum (m/z) 305 (M+), 273, 248, 188, 55, exact mass calcd for C$_{16}$H$_{19}$NO$_5$ 305.1263, found 305.1264.

7: R$_f$=0.27 (20% ethyl acetate in hexanes); IR 2947, 1745, 1603, 1576, 1479, 1423, 1327, 1263, 1194, 1138, 1111, 1082, 1024, 831 cm$^{-1}$; $^1$H NMR (500 MHz)$\delta$7.11 (d, 1 H, J=8.6 Hz), 6.62 (d, 1 H, J=8.6 Hz), 5.42-5.43 (m, 1 H), 3.92 (s, 3 H), 3.76 (s, 3 H), 3.36-3.42 (m, 2 H), 3.18 (d, 1H, J=18.2 Hz), 3.15 (m, 1 H), 2.13 d, 1H, J=17.5 Hz) 1.60 (s, 3 H), $^{13}$C NMR$\delta$207.5, 171.4, 163.2, 150.7, 137.7, 133.6, 126.4, 123.8, 109.6, 60.1, 53.4, 52.7, 46.9, 46.0, 40.4, 22.3; mass spectrum (m/z) 287 (M+), 255, 228, 200, 184, exact mass calcd for C$_{16}$H$_{17}$NO$_4$ 287.1158, found 287.1157.

8 (Z-olefin); R$_f$=0.39 (20% ethyl acetate in hexanes); IR 2909, 1732, 1601, 1578, 1558, 1475, 1423, 1321, 1252, 1205, 1151, 1111, 1086, 1030, 1003, 902, 827, 735, 638 cm$^{-1}$; $^1$H NMR $\delta$7.09 (d, 1 H, J=8.5 Hz), 6.54 (d, 1 H, J=8.6 Hz), 5.51 (q, 1 H, J=7.3 Hz , 5.40-5.42 m, 1 H), 3.89 (s, 3 H), 3.71 (s, 3 H), 2.99-3.19 (m, 3 H), 2.81 (d, 1 H, J=16.5 Hz); 2.21 (d, 1 H, J=17.0 Hz , 1.57 (s, 3 H), 1.51 (d, 1 H, J=16.5 Hz); 2.21 (d, 1 H, J=17.0 Hz), 1.57 (s, 3 H), 1.51 (d, 3 H, J=7.3 Hz); mass spectrum (m/z) 299 (M+), 240, 57, exact mass calcd for C$_{18}$H$_{21}$NO$_3$ 299.1521, found 299.1521.

Acid from 9: R$_f$=0.39 (ethyl acetate); IR 2500-3500 (br), 2932, 2594, 1705, 1599, 1578, 1477, 1423, 1379, 1323, 1269, 1128, 1111, 1076, 1030, 956, 908, 823, 777, 760, 735, 681, 646 cm$^{-1}$; $^1$H NMR$\delta$7.25 (d, 1 H, J=8.5 Hz), 6.57 (d, 1 H, J=8.5 Hz), 5.40-5.42 (m, 1 H), 5.31 (q, 1 H, J=6.7 Hz), 3.89 3.89 (s, 3 H), 3.62 (m, 1 H), 2.84-3.12 (m, 3 H), 2.18 (d, 1 H, J=17.0 Hz); 2.74 (d, 3 H, J=6.8 Hz), 1.54 (s, 3 H), 2.18 (d, 1 H, J=17.0 Hz); 2.74 (d, 3 H, J=6.8 Hz), 1.54 (s, 3 H); mass spectrum (m/z) 285 (M+), 240, 84, exact mass calcd for C$_{17}$H$_{19}$NO$_3$ 285.1365, found 285.1365.

10: R$_f$=0.15 (20% ethyl acetate in hexanes); IR 3331 (br), 2930, 1716, 1597, 1581, 1558, 1522, 1475, 1421, 1321, 1304, 1257, 1103, 1068, 1032, 914, 827, 777, 733 cm$^{-1}$; $^1$H NMR$\delta$7.56 (d, 1 H, J=8.6 Hz , 6.55 (d, 1 H, J=8.6 Hz , 5.54-5.56 (m, 1 H), 5.36 (q, 1 H, J=6.8 Hz), 4.98 (s, —NH), 3.88 (s, 3 H), 3.66 (br.s, 1 H), 3.62 (s, 3 H) 3.07 (br. d, 1 H, J=17.4 Hz), 2.82 (dd, 1 H, J=16.7, 1.6 Hz), 2.57 (br. d, 1 H, J=15 Hz), 2.23 (d, 1 H, J=15.6 Hz), 1.72 (d, 3 H, J=6.8 Hz), 1.51 (s, 3 H); mass spectrum 314 (M+), 224, 84, 69, exact mass calcd for C$_{18}$H$_{22}$N$_2$O$_3$ 314.1630, found 314.1630.

Synthetic Huperzine-A: R$_f$=0.10 (basic SiO$_2$, CHCl$_3$-Acetone-MeOH: 50/45/5); IR 3277, 2928, 1655, 1616, 1558, 1458, 1406, 1377, 1306, 1174, 1118, 912, 833, 769, 731, 659 cm$^{-1}$; $^1$H NMR$\delta$12.42 (br. s, pyridone —NH), 7.90 (d, 1 H, J=9.3 Hz), 6.42 (d, 1 H, J=9.6 Hz), 5.49 (q, 1 H, J=6.7 Hz), 5.42 (m, 1 H), 3.61 (m, 1 H), 2.89 (dd, 1 H, J=16.8, 5.1 Hz), 2.70 (d, 1 H, J=15.9 Hz), 2.14 br. s, 2 H), 1.68 (d, 3 H, J=6.6 Hz), 1.61 (br. s, —NH$_2$), 1.55 (s, 3 H); mass spectrum (m/z) 242 (M+), 227, 187, 57, exact mass calcd for C$_{15}$H$_{18}$N$_2$O 242.1419, found 242.1419.

6.2 EXAMPLE II

Biological Activity of Huperzine A and the 1-Carbon Analog of Huperzine A

The ability of natural huperzine A and synthetic racemic huperzine A, and the propylidene compound (general formula IV, R$_4$$^3$=R$_4$$^4$=CH$_3$, R$_4$$^5$=R$_4$$^6$=R$_4$$^4$=H, n=1, p=0, with a double bond between carbon 8 and carbon 15), which is the 1-carbon analog of huperzine A, to inhibit the cholinesterase enzymes was determined.

METHOD

Rats were killed by decapitation and the brains were rapidly extirpated. The cortex was dissected out on ice according to the method of Glowinski and Iversen. (See *J. Neurochem.* 13, 655 (1966)). Samples were homogenized in ice cold 0.32M sucrose. Homogenates were Centrifuged at 1000×g for 10 minutes to remove cell nuclei and heavy debris. The supernatant was then aspirated off and spun again (12000×g) for 20 minutes to form a pellet (Whittaker's P$_2$ fraction) containing synaptosomes and mitochondria. See E. G. Gray et al., *J.*

*Anatomy,* 96,70(1962). The pellet was resuspended in 0.32M sucrose. A portion of this synaptosome-rich fraction was added in triplicate to ice-cold pH 7.4 Krebs-Ringer medium.

Assay of acetylcholinesterase was carried out according to the method of Johnson and Russell. See C. D. Johnson et al., *Anal Biochem.*, 64,229(1978). Acetylcholine labelled in the acetate moiety was enzymatically hydrolyzed by incubation for 10 minutes at room temperature in the presence of the above synaptosome-rich fraction containing endogenous acetylcholinesterase enzyme. The reaction was terminated by addition of a "stopping mixture" containing chloroacetic acid (1.0M), sodium hydroxide (0.5M) and sodium chloride (2.0M) to the reaction vial. Toluene-based scintillation fluid was added to the vial, to extract the released labelled acetate into the organic phase. Under these conditions the unhydrolyzed labelled acetylcholine remains unextracted in the small aqueous reaction volume from which its weak beta-particles of decay do not escape to excite the scintillator. Thus, the sample can be counted directly in the same reaction vial, in which the hydrolysis of sample by acetylcholinesterase has occurred.

Inhibition of cholinesterase activity was estimated, in triplicate, in the presence of a wide range of concentrations ($10^{-9}$ to $10^{-3}$M).

RESULTS

The results are shown in Table I.

TABLE I

| EXTENT OF CHOLINESTERASE ENZYME INHIBITION | | | |
| --- | --- | --- | --- |
| Structural Name Synthesized | M.W. | $IC_{50}$ | $IC_{50}/IC_{50}$ of Huperzine A* |
| Natural Huperzine A | 242 | $10^{-7}$M | — |
| Synthesized Huperzine A | 242 | $6 \times 10^{-7}$M | 1.0 |
| 1-carbon Analog | 256 | $10^{-4}$M | 166.6 |

*The smaller this number, the more potent the compound.

As shown in Table 1, synthetic racemic huperzine A had an $IC_{50}$ of $6 \times 10^{-7}$M. This was very similar to the $IC_{50}$ value of natural huperzine A ($10^{-7}$M). Also, the 1-carbon analog inhibited the cholinesterase enzyme, but to a lesser extent than huperzine A.

What is claimed is:

1. Racemic huperzine A.

* * * * *